US008841627B2

(12) United States Patent
Li et al.

(10) Patent No.: US 8,841,627 B2
(45) Date of Patent: Sep. 23, 2014

(54) METHOD FOR IMAGING OBJECT USING PHOTONEUTRON TRANSMISSION AND DETECTOR ARRAYS USING THE SAME

(75) Inventors: Yuanjing Li, Beijing (CN); Yigang Yang, Beijing (CN); Tiezhu Li, Beijing (CN); Qinjian Zhang, Beijing (CN); Bin Wu, Beijing (CN); Hong Wang, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 187 days.

(21) Appl. No.: 13/519,907

(22) PCT Filed: Jun. 13, 2010

(86) PCT No.: PCT/CN2010/000855
§ 371 (c)(1),
(2), (4) Date: Sep. 24, 2012

(87) PCT Pub. No.: WO2011/079488
PCT Pub. Date: Jul. 7, 2011

(65) Prior Publication Data
US 2013/0026383 A1    Jan. 31, 2013

(30) Foreign Application Priority Data
Dec. 29, 2009   (CN) .......................... 2009 1 0244358

(51) Int. Cl.
*G01N 23/05*    (2006.01)
(52) U.S. Cl.
CPC ...................................... *G01N 23/05* (2013.01)
USPC ..................................................... 250/390.02

(58) Field of Classification Search
CPC ........ G01T 3/00; G01N 23/05; G01N 23/005; G01N 23/09; G01N 23/222; G01N 23/227; G21K 1/025
USPC ........................................ 250/390.01–390.12
See application file for complete search history.

(56) References Cited

U.S. PATENT DOCUMENTS 4,200,491 A  *  4/1980  Ball .............................. 376/254
5,028,789 A     7/1991  Whittemore
(Continued)

FOREIGN PATENT DOCUMENTS

| CN | 101329283 A | 12/2008 |
|---|---|---|
| CN | 201184870 Y | 1/2009 |
| CN | 201286192 Y | 8/2009 |
| RU | 2362148 C1 | 7/2009 |

OTHER PUBLICATIONS

Yang et al., "Explosive detetion using photoneutrons produced by X-rays", 2007, Nuclear Instruments and Methods in Physics Research A, vol. 579, pp. 400-403.*

(Continued)

*Primary Examiner* — Kiho Kim
(74) *Attorney, Agent, or Firm* — Marshall, Gerstein & Borun LLP

(57) ABSTRACT

A method for imaging an object by means of photoneutron transmission is provided. The method determines the position of the photoneutron rays based on the position of a neutron collimator, to overcome the problem of incapability of imaging due to loss of position information of the photoneutrons during moderation thereof. The method also images the object by arranging detector module arrays.

27 Claims, 4 Drawing Sheets

(56) References Cited

U.S. PATENT DOCUMENTS

| | | | |
|---|---|---|---|
| 5,838,759 A * | 11/1998 | Armistead | 378/57 |
| 2003/0048864 A1 * | 3/2003 | Akers | 376/157 |
| 2003/0155530 A1 * | 8/2003 | Adnani et al. | 250/491.1 |
| 2010/0243874 A1 | 9/2010 | Kang et al. | |

OTHER PUBLICATIONS

International Search Report in International Application No. PCT/CN2010/000855, dated Aug. 26, 2010 (with English translation).

* cited by examiner

METHOD FOR IMAGING OBJECT USING PHOTONEUTRON TRANSMISSION AND DETECTOR ARRAYS USING THE SAME

CROSS-REFERENCE TO RELATED APPLICATIONS

This application is the U.S. national phase of International Application No. PCT/CN2010/000855, filed Jun. 13, 2010, which claims the benefit of Chinese Patent Application No. 200910244358.8, filed Dec. 29, 2009.

TECHNICAL FIELD

The present invention generally relates to a method for imaging an object by means of photoneutron transmission generated by an accelerator and detector arrays using the same.

BACKGROUND ART

X-ray imaging techniques are widely applied in the security inspection field. Generally, X-rays are generated by utilizing electron beams provided by an electron accelerator to impinge on an electronic target. However, only a small portion of the generated X-rays is used for imaging. As such, at the time of X-ray imaging, it can easily occur to people to generate photoneutrons by way of X-rays impinging on a photoneutron target for the purpose of object imaging by means of transmission of photoneutron through the object. Since the behavioral property of photoneutrons in the object is different from that of X-rays, recognition of the object can be improved using two different imaging techniques.

However, photoneutrons are generated together with a large number of X-rays such that the measurement of photoneutrons will be interfered by X-rays, so it is infeasible to measure the photoneutrons by way of fast neutron detection directly. Photoneutrons must be moderated and then measured by a thermal neutron detector. Position information of the photoneutron rays has to be obtained upon imaging by means of photoneutron transmission. Generally speaking, position information of the rays depends on the size and position of the detector. However, during moderation of the photoneutrons, the photons have been diffused and the position information thereof has been lost when the photons had finally been measured. In this case, imaging is impossible. The present invention provides a solution to this problem so as to obtain a two-dimensional imaging of the detected object using the photoneutrons.

SUMMARY OF THE INVENTION

One aim of the present invention is to provide a method for imaging an object by means of photoneutron transmission. The method determines the position of the photoneutron rays passing through the object based on the position of a neutron collimator, so as to overcome the problem of incapability of imaging due to loss of position information of the photoneutrons during moderation thereof.

Another aim of the present invention is to provide a detector array which is capable of detecting photoneutron ray beams coming from the detected object so as to form a corresponding image. The detector can also provide a full image of the object by increasing the number of the detector arrays.

One aim of the present invention can be achieved by the following solutions. A method for imaging an object by means of photoneutron transmission, which uses photoneutron rays to irradiate the object, comprises the steps of: collimating the photoneutron rays passing through the object by means of a neutron collimator so as to determine the position information of the photoneutron rays based on the position of the neutron collimator; detecting the collimated photoneutron ray beams by means of a detector module, wherein the detector module includes a neutron moderator and at least one thermal neutron detector located within the neutron moderator, wherein the neutron moderator converts the photoneutrons into thermal neutrons, and wherein the thermal neutron detector measures the thermal neutrons so as to obtain attenuation information of the photoneutron ray beams upon passing through the object; and integrating the position information and the attenuation information so as to form an image of the corresponding part of the object.

As a preferred embodiment of the above method, the detector module and the neutron collimator make up of a detector array, wherein the number of the detector modules in each array corresponds to the number of slots so as to measure the photoneutron ray beam passing through each slot. There are multiple detector arrays, wherein each array includes a plurality of the detector modules, and the arrays are mutually staggered to ensure that the detector modules can detect the imaging information of every part of the object. Increasing the number of the detector arrays overcomes the problem of incapability of providing a complete image of a single detector array, due to the influence of the moderator which volume is larger than a single pixel, thereby providing the complete image of the object.

Another aim of the present invention can be achieved by the following solutions. A detector array for imaging an object by means of photoneutron transmission comprises detector modules, and a neutron collimator for determining the position information of the photoneutrons entering each of the detector modules via the neutron collimator, wherein the detector module includes a neutron moderator and at least one thermal neutron detector located within the neutron moderator, the neutron moderator converts the photoneutrons into thermal neutrons, and the thermal neutron detector measures the thermal neutrons so as to obtain attenuation information of the photoneutron rays upon passing through the object.

To obtain a complete image of the object, the number of the detector arrays can be increased, and meanwhile the arrays are mutually staggered such that the photoneutron ray beams measured by each of the detector modules are not overlapped with each other.

Other aims and advantages of the present invention will become apparent by reading the following detailed description with reference to the drawings.

DETAILED DESCRIPTION OF THE PREFERRED EMBODIMENTS

Figure 1:
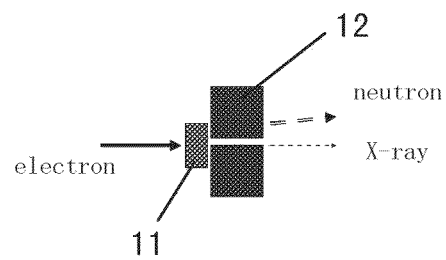
FIG. 1 is a schematic view showing the generation of photoneutrons.

FIG. 1 shows a manner to generate photoneutrons. As shown, an electron beam provided by an electron accelerator impinges an electron target 11 to generate X-rays, and X-rays impinge a photoneutron conversion target 12 to generate photoneutrons. Commonly-used photoneutron target materials are all nuclides having a low photoneutron threshold, such as $^9$Be and $^2$H. Therefore, Be target and heavy water target are usually used as a neutron conversion body, wherein the reaction type of the Be target can be represented as follows:

$$\gamma + {}^9Be \rightarrow {}^8Be + n, \text{threshold}: 1.67 \text{ MeV} \quad (1)$$

wherein, γ means a photon, n means a neutron, and the energy of the neutron is decided by the difference between the energy of the photon and the reaction threshold. The reaction type of the heavy water target can be represented as follows:

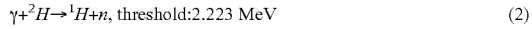

$$\gamma + {}^2H \rightarrow {}^1H + n, \text{threshold}: 2.223 \text{ MeV} \quad (2)$$

It can be known from the above formulae (1) and (2) that the photoneutrons are generated together with X-rays. It is usually deemed that the photoneutrons are generated at the same time of the generation of the X-rays.

Such photoneutrons have energy in the range of hundreds of keV to a few MeV (which is specifically determined by the energy of the accelerator) and therefore belong to fast neutrons. Even though the photoneutron conversion target functions to shield the X-rays to some extent, there is still a large number of X-rays accompanying the photoneutrons. If a neutron detector is used to directly detect such photoneutrons, a large number of X-rays will also enter the neutron detector. The photoneutrons and X-rays are generated simultaneously, and the electron accelerator works in a pulse status with a pulse width of μs order, and also the photoneutrons and X-rays simultaneously fly to the neutron detector from the photoneutron conversion target in a short time (usually less than 1 μs), so the neutron detector will measure X-rays while measuring neutrons. There are numerous X-rays entering the neutron detector, which typically have more than 4 orders, so no matter how insensitive the neutron detector is to the X-rays, the X-rays will form a huge signal in the neutron detector, and such a signal significantly exceeds the signal formed by the neutrons in the neutron detector, such that the measurement of photoneutrons is severely interfered, thereby causing the neutron detector incapable of obtaining information on the photoneutrons.

It has been known that the X-rays and the photoneutrons have different properties in a substance:

The X-rays will be absorbed by the substance after a few times of impingement, and the X-rays can stay in the substance only for the ns order, in such a way that the interference in the photoneutron measurement caused by the X-rays is solved;

The photoneutrons will be absorbed by the substance after a numerous times of impingement. The times of impingement of the photoneutrons vary from dozens of times to thousands of times, and the duration thereof varies from a few μs to dozens of ms based on the different materials of the substances.

It can be known from the different behavioral properties of the two rays that a suitable neutron moderating structure must be arranged to moderate the neutrons in the moderator. It usually takes more than a few μs to moderate the photoneutrons from fast neutrons to thermal neutrons, so X-ray pulses had already died away when the photoneutrons are moderated to the thermal neutrons. At this time, a thermal neutron sensitive detector is used to measure the moderated photoneutrons so as to obtain information on the photoneutrons without the interference of X-rays.

However, because the photoneutrons will lose position information during moderation, a method for imaging an object by means of photoneutron transmission of the present invention considers determining the position information of rays based on the position of the neutron collimator.

Figure 2:
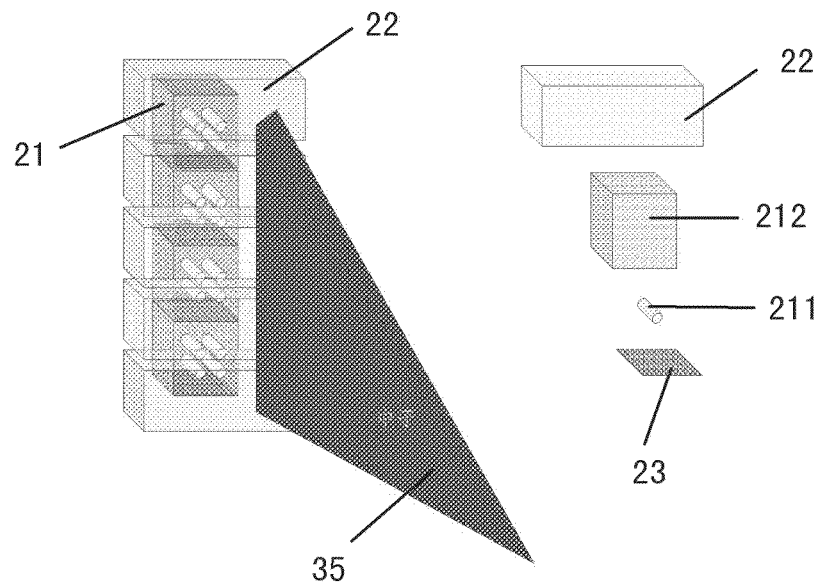
FIG. 2 is a schematic view showing neutron position discrimination achieved by means of a neutron collimator.

FIG. 2 shows a schematic view showing photoneutron position discrimination achieved by the neutron collimator. As shown, a beam of photoneutrons has already been collimated as a sector via the collimator 61 (see FIG. 6) for transmission imaging. FIG. 2 shows four neutron detector modules 21 arranged in one array. Of course, the four neutron detector modules are used for illustration only and by no way intended to limit the present invention. The actual number of the detector modules is determined as actually required, for instance, according to the area of the detected object and the desired resolution. Each detector module has four thermal neutron detectors 211. Similarly, the four thermal neutron detectors herein are used for illustration only and by no way intended to limit the present invention. The number of the thermal neutron detectors is determined according to the desired sensitivity. The more the thermal neutron detectors are, the higher the sensitivity is. Hence, there may be one thermal neutron detector at least, or possibly six or eight, etc. The thermal neutron detectors 211 are located within and fully enclosed by the neutron moderator 212. The neutron moderator enables the fast neutrons to decelerate therein to produce a time lag, until the thermal neutrons are formed so as to be detected by the thermal neutron detector. Since the position information of the neutrons will be lost during moderation, the position information thereof cannot be determined based on the position of the detector, i.e., imaging is impossible. A neutron shield 22 for collimating the photoneutron rays is employed for imaging. FIG. 2 shows five neutron shields 22 for collimation, and these neutron shields and the detector modules together form a single detector array. It should be explained that the number (five) herein is used for illustration only and by no way intended to limit the present invention. There may be any number (more than two) of neutron shields 22 for collimation according to scanning requirement. The five neutron shields for collimation form four horizontal slots 31 (see FIG. 3) which are parallel to and identical to each other. The width of the slot depends on the user's need, for example, the desired pixel size. As an embodiment of the method of the present invention, the present invention is described using 5 cm as a typical value of the width of the slot. The four slots intersect with the sector photoneutron beam 25 to obtain four photoneutron beam lines—each photoneutron beam line is a straight line emitted from the photoneutron conversion target and therefore has good directionality. The four neutron beam lines enter the four neutron detector modules in FIG. 2 respectively and are then moderated and measured thereby. Thermal neutron absorbers 23 are arranged between the detector modules 21 to absorb the thermal neutrons which are to enter the adjacent detector modules. This aims to prevent the neutrons entering different modules from crosstalk between the modules, i.e., one detector module can only measure the neutrons ejected therein. To this end, it is required that the neutron moderator of each detector must have a certain size so as to allow the neutrons to be sufficiently moderated, such that the energy of the neutrons has been low enough in an attempt to enter the adjacent detector module so as to be sufficiently shielded by the thermal neutron absorbers 23. The size is usually large than 10 cm. We will take 20 cm as an example for discussion. The neutrons have position information prior to incidence into the detector module designed in the above manner. Even though the neutrons lose the position information due to moderation after ejection into the detector module, the measurement result can still reflect the incidence position of the rays because each detector module 21 can only measure the neutrons ejected in a determined direction.

Moreover, the neutron moderator 212 also shields the thermal neutrons in the ambient environment so as to prevent the thermal neutrons in the ambient environment from interference in the above measurement.

Figure 3:
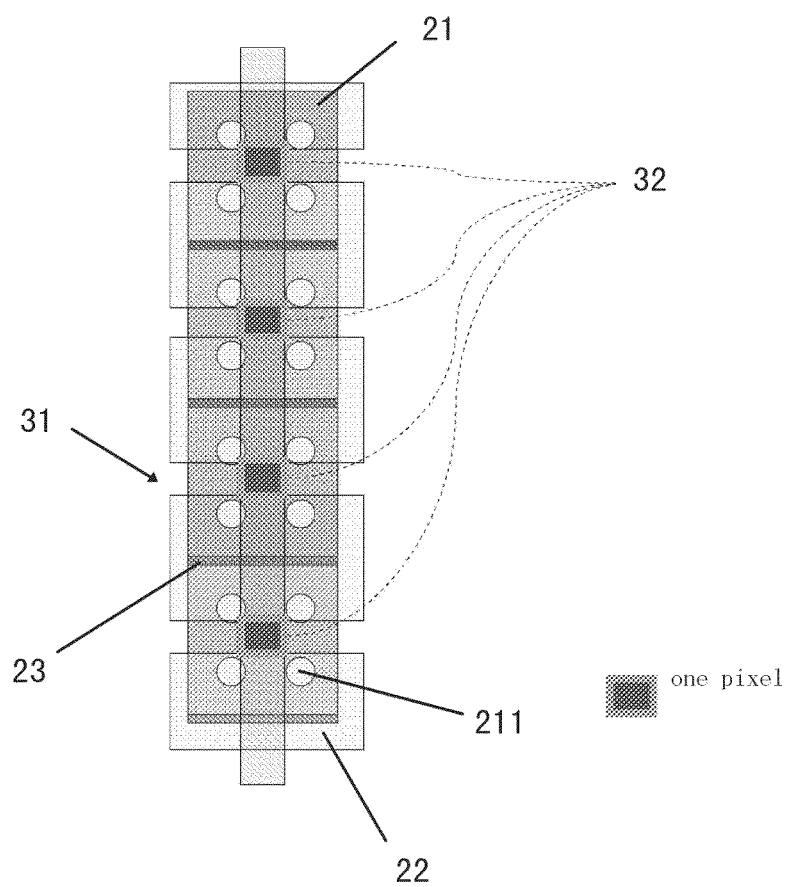
FIG. 3 is a schematic view showing the spatial loss caused by a moderator upon imaging a single pixel.

FIG. 3 further shows a schematic view showing photoneutron position discrimination achieved by the neutron collimator. As shown in FIG. 3, "four" photoneutron beams respectively irradiate four small pixels 32, and the photoneutron beam lines passing through the small pixels 32 respectively enter four detector modules 21 via the slots 31, and are moderated and measured in the detector module. In such a manner, the array composed of the four detector modules 21 can image the "four" photoneutron beam lines using the position information and attenuation information of the photoneutrons. Since more detector modules can be arranged, the eigen detecting efficiency can be guaranteed.

Figure 4:
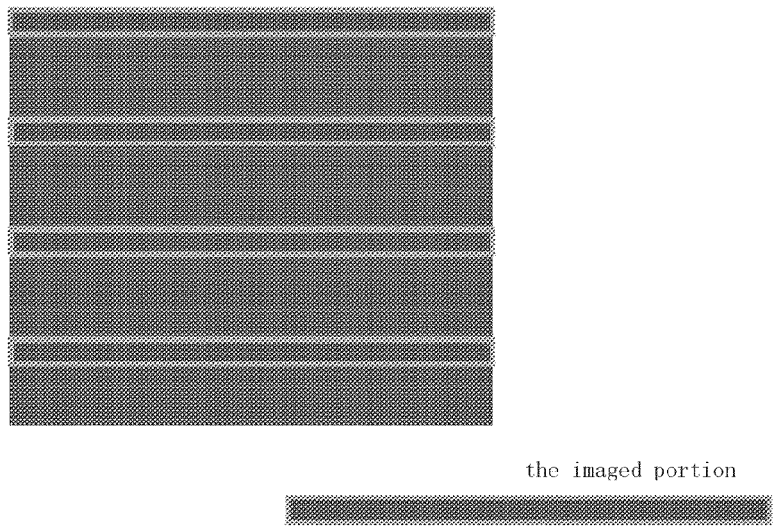
FIG. 4 shows an image of ¼ area of an object provided by a single array of detector modules.

However, as shown in FIG. 3, in order to prevent the crosstalk between the photoneutrons coming from different directions, the moderator of each detector module must have a size that is large enough, which is usually required to be larger than 10 cm. The effective size thereof is 20 cm (width)×20 cm (height), with a length larger than 20 cm. Suppose each neutron beam line has a cross section of 5 cm×5 cm, then it means a space of 20 cm×20 cm is needed for each neutron beam line of 5 cm×5 cm, such that 75% of the neutron beam lines cannot be measured. Even though the aim as shown in FIG. 2 is achieved, only a partial image of the object can be obtained after the object is scanned. As shown in FIG. 4, if each pixel is 5 cm×5 cm, and the size of the neutron moderator is 20 cm×20 cm×20 cm, only ¼ of the object can be imaged each time.

Figure 5:
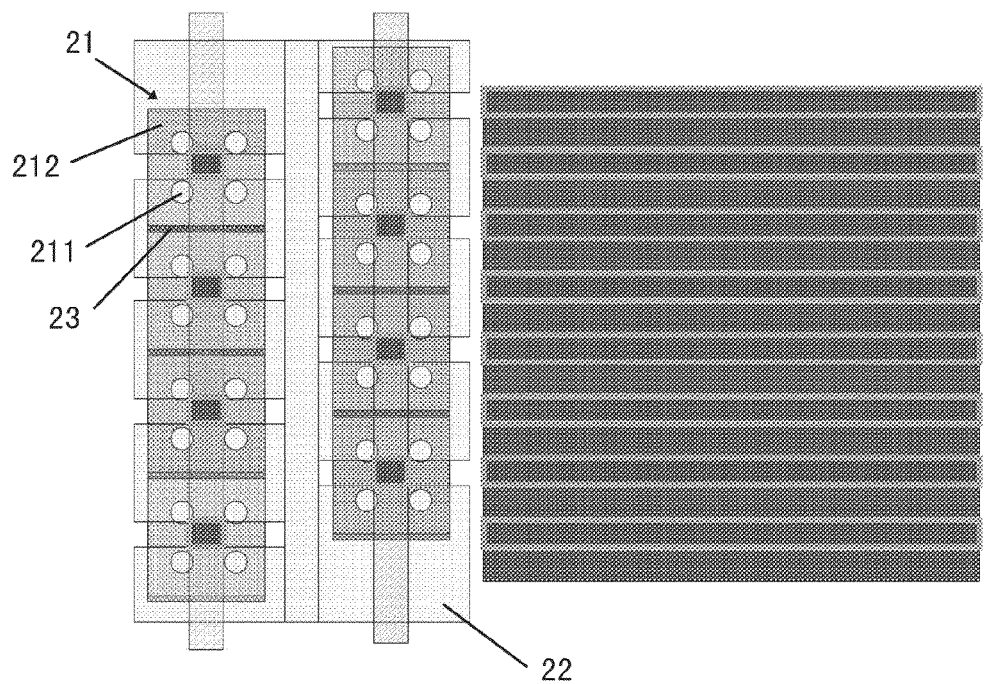
FIG. 5 shows an image of ½ area of the object provided by two arrays of detector modules.

If there are multiple detector arrays and the arrays are mutually staggered, the whole object can be imaged. As shown in FIG. 5, two detector arrays as shown in FIG. 3 are employed. The two detector arrays are completely the same, i.e., both include four detector modules 21 and five neutron shields for collimation. However, the two arrays are staggered up and down by 10 cm so as to ensure that the photoneutron ray beams measured by each detector module are not overlapped with each other. Namely, it is impossible for two or more detector modules to detect the photoneutron beams coming from the same portion of the object. In such a way, the two arrays of the detector modules respectively scan ¼ area of the object, and together ½ area of the object.

Figure 6:
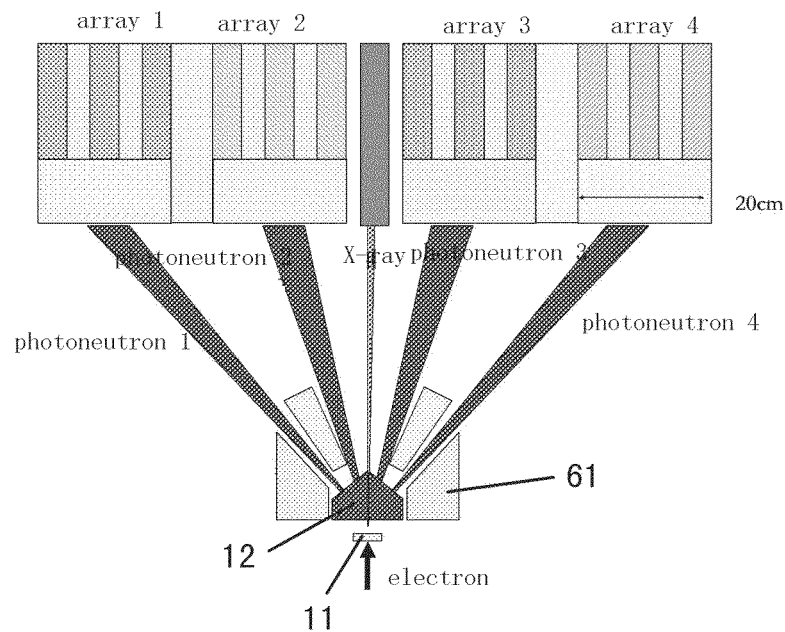
FIG. 6 shows the scanning of the object by four arrays of detector modules.
Figure 7:
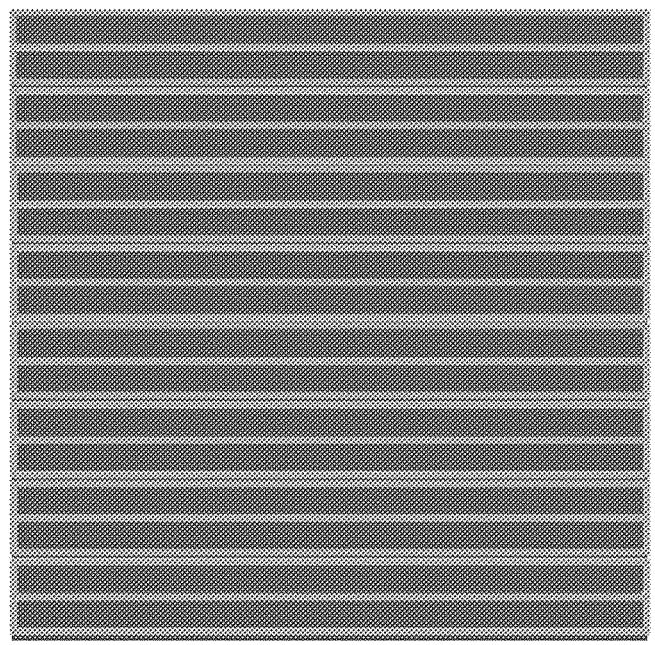
FIG. 7 shows an image of the full area of the object provided by the four arrays of detector modules.

By analogy, two more arrays of detectors can be added for scanning the full area of the object. The actual number of the detector arrays is determined based on the area of the detected object and the desired pixel. FIG. 6 shows the full image using the photoneutron transmission imaging by four phononeutron detector arrays. FIG. 6 (a top view) shows four photoneutron detector arrays which are symmetrically distributed at both sides of the X-ray beam respectively, wherein the photoneutron detector arrays 1 and 2 are located as shown in FIG. 5, and the photoneutron detector arrays 3 and 4 are the same as them, but only on the other symmetrical side of the main X-ray beam. The photoneutron detector arrays 3 and 4 are displaced 5 cm from the photoneutron detector arrays 1 and 2 in an up-and-down direction (namely, a direction perpendicular to the drawing in the paper). The full image of the detected object can be scanned using the four detector arrays, i.e., the full image of the object can be achieved by splicing the images obtained by the four detector arrays, as shown in FIG. 7.

What needs explanation is that the four detector arrays in FIG. 6 are placed differently and the neutron beams are oriented differently such that the neutrons follow different paths upon passing through the detected object, thereby resulting in that the images obtained by the four detector modules may not match each other to some extent. To solve this problem, the distance between the four detector arrays must be made as small as possible. 20 cm is a feasible solution according to the schematic view of the present invention. 15 cm is also feasible if designed carefully. Even though the images may still not match each other, the matching of the images is within an acceptable range because the resolution of the neutron imaging is about 5 cm.

Although the typical embodiments of the present invention have been described, it should be appreciated that the present invention is not limited to these embodiments. As far as those skilled in the art are concerned, various modifications and improvements of the present invention can be achieved without departing from the spirit and scope of the claims of the present invention.

The invention claimed is:

1. A method for imaging an object by means of photoneutron transmission, which uses photoneutron rays to irradiate the object, characterized by comprising the steps of:
    collimating the photoneutron rays passing through the object by means of a neutron collimator so as to determine the position information of the photoneutron rays based on the position of the neutron collimator;
    detecting the collimated photoneutron ray beams by means of a detector module, wherein the detector module includes a neutron moderator and at least one thermal neutron detector located within the neutron moderator, wherein the neutron moderator converts the photoneutrons into thermal neutrons, and wherein the thermal neutron detector measures the thermal neutrons so as to obtain attenuation information of the photoneutron ray beams upon passing through the object; and
    integrating the position information and the attenuation information so as to form an image of the corresponding part of the object.

2. The method according to claim 1, wherein the neutron collimator consists of a plurality of neutron shields, and the adjacent ones of the plurality of neutron shields form slots therebetween, through which slots the photoneutron rays pass to form the collimated photoneutron ray beams.

3. The method according to claim 2, wherein the size of the slot is determined based on the desired pixel.

4. The method according to claim 2, wherein the detector module and the neutron collimator comprise a detector array, wherein the number of the detector modules in each array corresponds to the number of slots so as to measure the photoneutron ray beam passing through each slot.

5. The method according to claim 4, wherein that there are multiple detector arrays, wherein each array includes a plurality of the detector modules, and wherein the arrays are mutually staggered to ensure that the photoneutron ray beams detected by each of the detector modules are not overlapped with each other.

6. The method according to claim 5, wherein the distance between the detector arrays must be small enough so that the matching of the images generated by the arrays is within an acceptable range.

7. The method according to claim 5, wherein the images obtained by each array of the detector modules are spliced to provide a full image of the object.

8. The method according to claim 5, wherein the number of the detector arrays is determined based on the area of the object and the desired pixel.

9. The method according to claim 4, wherein the detector array further includes thermal neutron absorbers arranged between the adjacent detector modules to absorb the thermal neutrons which are to enter the adjacent detector modules.

10. The method according to claim 1, wherein the neutron moderator has a size that is large enough to sufficiently moderate the photoneutrons, thereby preventing the crosstalk between the thermal neutrons in the adjacent detector modules.

11. The method according to claim 10, wherein the neutron moderator has a size that is larger than 10 cm.

12. The method according to claim 1, wherein the neutron moderator can shield the thermal neutrons in the ambient environment so as to prevent interference in the measurement.

13. The method according to claim 1, wherein the more the thermal neutron detectors are, the higher the sensitivity of the detector module is.

14. The method according to claim 1, wherein the photoneutron rays are generated by X-rays impinging on a neutron conversion target.

15. The method according to claim 1, wherein the photoneutron rays are collimated by the neutron collimator prior to their entry into the object.

16. A detector array for imaging an object by means of photoneutron transmission, comprising a detector module, wherein the detector array further includes a neutron collimator for determining the position information of the photoneutrons entering each of the detector modules via the neutron collimator, wherein the detector module includes a neutron moderator and at least one thermal neutron detector located within the neutron moderator, wherein the neutron moderator converts the photoneutrons into thermal neutrons, and wherein the thermal neutron detector measures the thermal neutrons so as to obtain attenuation information of the photoneutron rays upon passing through the object.

17. The detector array according to claim 16, wherein the neutron collimator consists of a plurality of neutron shields, and wherein the adjacent ones of the plurality of neutron shields form slots therebetween, through which slots the photoneutron rays pass to form the collimated photoneutron ray beams.

18. The detector array according to claim 17, wherein the number of the detector modules in each array corresponds to the number of slots so as to measure the photoneutron ray beam passing through each slot.

19. The detector array according to claim 16, wherein there are multiple detector arrays, and wherein the arrays are mutually staggered to ensure that the photoneutron ray beams measured by each of the detector modules are not overlapped with each other.

20. The detector array according to claim 19, wherein the distance between the detector arrays must be small enough so that the matching of the images of the arrays is within an acceptable range.

21. The detector array according to claim 16, wherein the detector array provides an image of the full area of the object by adding more arrays.

22. The detector array according to claim 16, wherein the detector array further includes thermal neutron absorbers arranged between the adjacent detector modules to absorb the thermal neutrons which are to enter the adjacent detector modules.

23. The detector array according to claim 16, wherein the neutron moderator has a size that is large enough to sufficiently moderate the photoneutrons, thereby preventing the crosstalk between the thermal neutrons in the adjacent detector modules.

24. The detector array according to claim 23, wherein the neutron moderator has a size that is larger than 10 cm.

25. The detector array according to claim 16, wherein the neutron moderator can shield the thermal neutrons in the ambient environment so as to prevent interference in the measurement.

26. The detector array according to claim 16, wherein the number of the detector arrays is determined based on the area of the object and the desired pixel.

27. The detector array according to claim 16, wherein the more the thermal neutron detectors are, the higher the sensitivity of the detector module is.

* * * * *